United States Patent
Huang et al.

(10) Patent No.: US 10,494,628 B2
(45) Date of Patent: Dec. 3, 2019

(54) METHOD AND APPARATUS FOR ENRICHING PATHOGEN DNA

(71) Applicants: Yiwei Huang, Erlangen (DE); Divya Khandige Sharma, Bangalore/Karnataka (IN); Ragavendar Ms, Bangalore (IN); Nivedita Mitra, Bangalore (IN); Ramya Vutukuru, Karnataka (IN)

(72) Inventors: Yiwei Huang, Erlangen (DE); Divya Khandige Sharma, Bangalore/Karnataka (IN); Ragavendar Ms, Bangalore (IN); Nivedita Mitra, Bangalore (IN); Ramya Vutukuru, Karnataka (IN)

(73) Assignee: Siemens Healthcare GmbH, Erlangen (DE)

( * ) Notice: Subject to any disclaimer, the term of this patent is extended or adjusted under 35 U.S.C. 154(b) by 228 days.

(21) Appl. No.: 15/468,836

(22) Filed: Mar. 24, 2017

(65) Prior Publication Data
US 2017/0275613 A1    Sep. 28, 2017

(30) Foreign Application Priority Data
Mar. 24, 2016 (IN) .............................. 201631010299

(51) Int. Cl.
*C12N 15/10* (2006.01)
*B01L 3/00* (2006.01)
*C12Q 1/68* (2018.01)
*G01N 1/40* (2006.01)
*C12Q 1/6888* (2018.01)

(52) U.S. Cl.
CPC .......... *C12N 15/1013* (2013.01); *B01L 3/502* (2013.01); *C12Q 1/6888* (2013.01); *B01L 2300/087* (2013.01)

(58) Field of Classification Search
CPC . C12Q 1/6806; C12Q 1/6888; C12N 15/1013
See application file for complete search history.

(56) References Cited

U.S. PATENT DOCUMENTS 8,383,353 B2    2/2013  Stefas

*Primary Examiner* — David C Thomas
(74) *Attorney, Agent, or Firm* — Lempia Summerfield Katz LLC

(57) ABSTRACT

A method and apparatus for enrichment and detection of low abundance pathogens are provided. The method includes adding one or more proteins containing pathogen binding domains to the sample. The sample is incubated to form a complex thereby. The complex is separated from the sample, and an apparatus is provided for enriching pathogen DNA that achieves pathogen detection levels as low as 1 cfu/ml. The method further includes adding a lysis buffer to the separated complex and incubating to form a mixture. A buffer containing guanidine thiocyanate is added to the mixture. The mixture is connected with a matrix to form a bound entity, and the bound entity is separated from the mixture.

13 Claims, 2 Drawing Sheets

METHOD AND APPARATUS FOR ENRICHING PATHOGEN DNA

PRIORITY

This application claims the benefit of IN 201631010299, filed on Mar. 24, 2016, which is hereby incorporated by reference in its entirety.

FIELD

The present embodiments relate to enriching pathogen DNA from a given sample suspected to contain pathogens.

BACKGROUND

Currently, the method of enriching pathogen DNA is performed by adding to the given sample one or more proteins that have pathogen binding domains. The pathogen binding domains bind to the pathogens on incubation to form a complex. The complex formed between the proteins and the pathogens is then separated from the given sample.

The aforementioned method does not, however, achieve pathogen detection levels as low as 10 cfu/ml or lower.

SUMMARY OF THE INVENTION

The scope of the present invention is defined solely by the appended claims and is not affected to any degree by the statements within this summary.

The present embodiments may obviate one or more of the drawbacks or limitations in the related art. For example, a method and an apparatus of enriching pathogen DNA that achieves pathogen detection levels as low as 10 cfu/ml or lower are provided.

A lysis buffer is added to the separated complex and is incubating to form a mixture. A buffer containing guanidine thiocyanate is added to the mixture. The mixture is contacted with a matrix to form a bound entity. The bound entity is separated from the mixture.

A method of enriching pathogens from a given sample suspected of containing pathogen cells is provided. The method includes adding one or more proteins that contain pathogen binding domains to the given sample. Pathogen binding domains recognize and bind to cell surface receptors, such as proteins, etc. present on the cell surface of the pathogens, therefore forming a complex. Therefore, proteins with pathogen binding domains provide for easy separation of pathogens from the given sample. The method further includes incubating the sample to allow formation of complex between the proteins and the pathogens. The incubation is done for a time period ranging between 1 minute and 60 minutes (e.g., between 15 and 30 minutes). The method also includes separating complexes formed between the proteins and pathogens. Therefore, the pathogen fraction is enriched from the eukaryotic cells present in the sample.

According to one embodiment, the method further includes adding a lysis buffer to the separated complex and incubating the mixture. The lysis buffer lyses the pathogen cells, thereby releasing the pathogen DNA from the cells. The incubation may be done for a period ranging between 10 seconds and 60 minutes (e.g., between 3 minutes and 5 minutes). The pH of the lysis buffer is in the range between 6 and 8.

According to another embodiment, the method includes adding a buffer containing guanidine thiocyanate to the mixture formed. Guanidine thiocyanate is a chaotropic salt that is highly soluble in aqueous solutions.

According to yet another embodiment, the method further includes contacting the mixture with a matrix. The matrix binds to the released pathogen DNA in the mixture and forms a bound entity. The binding of the pathogen DNA to the matrix is reversible and may be due to interactions such as ionic interaction or by ligands, etc. The guanidine thiocyanate enables the capture of the nucleic acids with magnetic beads. The method further includes separating the bound entity from the mixture. Therefore, the pathogen DNA is enriched from the sample.

According to an embodiment, the proteins containing pathogen binding domains are chosen from a group consisting of innate immune proteins, acute phase proteins, and fusion proteins containing pathogen binding domains of innate and/or acute phase proteins. The innate immune proteins may be, for example, members of the complement system. Acute phase proteins may include, for example, mannose binding proteins, C-reactive proteins, etc. Fusion proteins are chimeric proteins that have parts of different proteins.

According to an embodiment, the one or more proteins are coated onto a substrate. The substrate is chosen from a group consisting of polystyrene beads and paramagnetic beads. This provides easier separation of the proteins from the sample once a complex between pathogens and the proteins are formed.

According to another embodiment, the complex is separated from the sample using a magnet. If the substrate onto which the one or more proteins are coated is a paramagnetic bead, the magnet attracts the paramagnetic bead, thereby separating the complex from the mixture.

According to yet another embodiment, the complex is separated from the sample by centrifugation. If the substrate onto which the one or more proteins are coated is a glass bead, the complex formed may be separated from the sample using centrifugation.

According to an embodiment, the lysis buffer is a composition of lithium acetate and sodium dodecyl sulphate. The lysis buffer lyses the pathogen cells bound to the substrate, thereby releasing the pathogen DNA.

According to yet another embodiment, the concentration of lithium acetate in the lysis buffer ranges from 0.01M to 0.5M.

According to another embodiment, the concentration of sodium dodecyl sulphate in the lysis buffer ranges from 0.1% to 5% v/v or w/v.

According to an embodiment, the matrix is a silica coated magnetic bead. The silica coated on the magnetic bead may be in the form of, for example, silica gel. The magnetic bead includes at least one particle of ferromagnetic, ferrimagnetic, supermagnetic or paramagnetic material. The surface of the magnetic bead is adsorptive and adheres only to DNA strands and not other components in the mixture. Silica binds to pathogen DNA in the presence of guanidine thiocyanate, therefore making the separation of pathogen DNA from the mixture easier. The concentration of guanidine thiocyanate is sufficiently high to cause the silica coated magnetic bead to bind to the pathogen DNA.

According to yet another embodiment, the complex is separated from the mixture using a magnet. The magnetic bead in the matrix is attracted to the magnet, thereby making the separation process of the complex easier.

According to an embodiment, the pathogen DNA from the bound entity is analyzed. Analysis of the pathogen DNA may be done by various methods, for example, amplification by polymerase chain reaction, or DNA sequencing, or direct nucleic acid detection.

One or more of the present embodiments also relate to an apparatus for enriching pathogen DNA from a given sample suspected to contain pathogen cells. The apparatus includes a sample chamber to which a reservoir that contains a binding buffer and one or more proteins containing pathogen binding domains is connected. The connection of the sample chamber to the reservoir allows the contact of the binding buffer and the one or more proteins in the reservoir with the sample that may be added in the sample chamber. According to one or more of the present embodiments, the apparatus further includes a lysis chamber to which a reservoir containing a lysis buffer is connected. In the lysis chamber, the pathogen cells are lysed by the lysis buffer in the reservoir.

According to a further embodiment, the apparatus includes a reservoir containing a lysis buffer having guanidine thiocyanate, and a matrix that is connected to the lysis chamber. According to an embodiment, the apparatus further includes an analysis chamber. Analysis of extracted pathogen DNA may be performed in the analysis chamber.

According to an embodiment, the sample chamber is adapted to receive a sample suspected to contain pathogen cells. The addition of the sample in the sample chamber of the apparatus may be done manually or may be automated.

According to yet another embodiment, the lysis chamber is configured to receive a complex formed between the one or more proteins containing pathogen binding domains and pathogen cells. When one or more proteins having pathogen binding domains come in contact with the sample having pathogen cells in the sample chamber, a complex is formed between the proteins and the pathogen cells. Such formed complex may be added into the lysis chamber in an automated way for further processing.

According to another embodiment, the analysis chamber is configured to receive a bound entity from the lysis chamber. The pathogen DNA released in the lysis chamber forms a bound entity with the matrix present in the reservoir. Such bound entities may be transferred into the analysis chamber in an automated way for further analysis of the pathogen DNA. Further analysis of DNA may include, for example, amplification of DNA, sequencing of DNA, etc.

DETAILED DESCRIPTION

Figure 1:
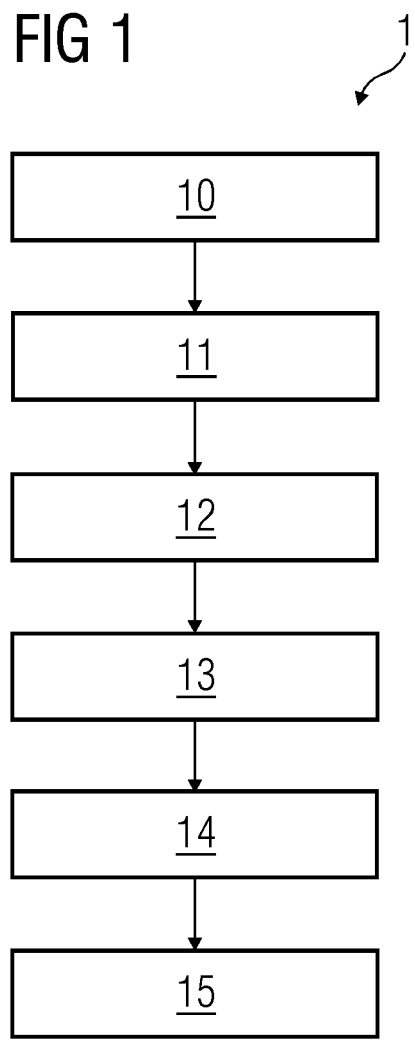
FIG. 1 illustrates a schematic diagram of a flow chart of an embodiment of a method.

Embodiments for carrying out one or more of the present embodiments are described in detail. The various embodiments are described with reference to the drawings, where like reference numerals are used to refer to like elements throughout. In the following description, for purpose of explanation, numerous specific details are set forth in order to provide a thorough understanding of one or more embodiments. Such embodiments may be practiced without these specific details.

FIG. 1 illustrates a schematic diagram of a flowchart of an embodiment of the method 1. The sample used in the present embodiment is whole blood suspected to contain pathogens. Alternatively, other fluids of the human body that are known to be used for such analyses may also be used. In act 10 of the method 1, a binding buffer is added to the sample, after which one or more proteins including pathogen binding domains are added to the sample. The plurality of proteins are coated onto a substrate. In the present embodiment, ApoH beads are used for demonstration. ApoH beads include ApoH proteins coated onto a micro-bead. The microbead in the present embodiment is a paramagnetic bead. ApoH protein is apolipoprotein H that has a capability to bind to micro-organisms due to the presence of pathogen binding domains. The mixture is incubated so as to allow formation of complex between ApoH proteins and pathogens in the sample. The incubation is done for a period ranging between 1 minute to 60 minutes (e.g., between 15 minutes and 30 minutes). The mixture is gently mixed to allow for binding of pathogens to pathogen binding proteins.

Once the complex is formed, in act 11 of the method 1, the beads are magnetically separated. In one separation, the beads are washed so as to remove any residual eukaryotic cells that may have been bound to the beads. In act 12 of the method 1, the complex is subjected to lysis buffer in order to lyse the pathogen cells. In the present embodiment, the lysis buffer is briefly heated at a temperature in the range between 50° C. and 90° C. for a time period in the range between 1 minute and 5 minutes. The lysis buffer is a composition of lithium acetate and sodium dodecyl sulphate (SDS) and has a pH in the range between 6 and 8. The concentration of lithium acetate varies from 0.01M to 0.5M (e.g., from 0.1M to 0.3M). The concentration of SDS varies from 0.1% to 5% v/v or w/v (e.g., from 0.5% to 2% v/v or w/v).

In act 13 of the method 1, a preheated lysis buffer containing guanidine thiocyanate is added to the mixture. In the present embodiment, the lysis buffer used is VERSANT® lysis buffer. To the mixture formed, matrix is added in act 14 of the method 1. Alternatively, instead of preheating the lysis buffer, the mixture may be heated once the lysis buffer containing guanidine thiocyanate and matrix are added. The matrix is a silica coated magnetic bead. The isolated pathogen DNA binds to the silica coated magnetic beads in the presence of guanidine thiocyanate and forms a bound entity. The mixture is vigorously vortexed to dislodge pathogen lysate from the beads. In act 15 of the method 1, the bound entities are separated from the mixture using a magnet. The beads bound to pathogen DNA may be directly subjected to quantitative PCR for quantification.

Figure 2:
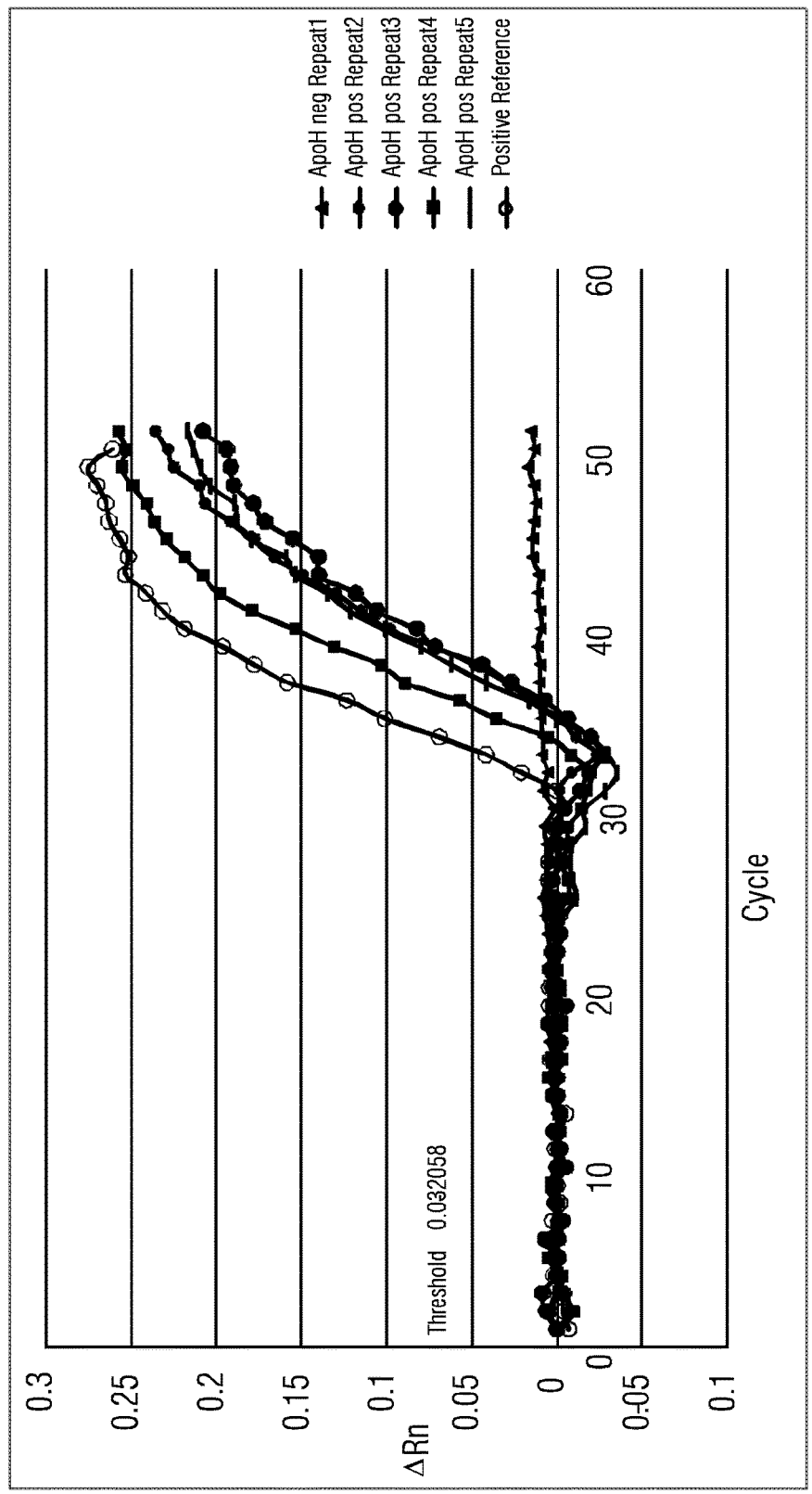
FIG. 2 illustrates a graph of the effect of positive enrichment on the detection of 1 cfu/ml *Candida tropicalis*.

FIG. 2 illustrates a graph of the effect of positive enrichment on the detection of 1 cfu/ml *Candida tropicalis*. The X-axis represents the number of amplification cycles, and the Y-axis represents the intensity of normalized fluorescence. For the experiment, 5.0 ml fresh blood, collected in EDTA vacutainers, is spiked with 5 cfu of *Candida tropicalis* in order to obtain blood sample with final concentration of 1 cfu/ml. 20 µl of ApoH protein beads is added to the blood and incubated in the range between 5 minutes and 20 minutes in order to achieve positive enrichment of the microbe. Following lysis and formation of the bound entity, the pathogen DNA was subjected to quantitative polymerase chain reaction (qPCR). The qPCR curves depicted on the graph indicate the effect of positive treatment with ApoH protein beads on the detection of 1 cfu/ml *Candida tropicalis*. The samples used in this experiment include a positive reference that has a no blood background, an unspiked blood sample treated with ApoH beads, and blood samples spiked with pathogens treated with ApoH based positive enrichment. Each sample was run in triplicates.

For the $Ct_{18s\ rDNA\ average}$, an average of 3 sample replicates for positive reference is 32.99 cycles, ApoH treated blood is 35.51 cycles, blood only treated with ApoH protein beads is undetermined, and negative template control is undetermined. Therefore, the method provides for detection of pathogen cells in the blood to a level as low as 1 cfu/ml.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method of enriching pathogen DNA from a given sample suspected of containing pathogens, the method comprising:
    adding one or more proteins containing pathogen binding domains to the sample;
    incubating the sample to form a complex thereby; and
    separating the complex from the sample;
    adding a lysis buffer to the separated complex and incubating to form a mixture, such that cells of the pathogens present in the mixture are lysed and the pathogen DNA is released into the mixture;
    adding a buffer containing guanidine thiocyanate to the mixture;
    contacting the mixture with a matrix to form a bound entity including the pathogen DNA from the mixture; and
    separating the bound entity from the mixture.

2. The method of claim 1, wherein the one or more proteins containing pathogen binding domains are chosen from a group consisting of innate immune proteins, acute phase proteins, and fusion proteins containing the pathogen binding domains of innate, acute, or innate and acute phase proteins.

3. The method of claim 2, wherein the one or more proteins are coated onto a substrate chosen from a group consisting of glass beads and paramagnetic beads.

4. The method of claim 1, wherein separating the complex from the sample comprises separating the complex from the sample using a magnet.

5. The method of claim 1, wherein separating the complex from the sample comprises separating the complex from the sample by centrifugation.

6. The method of claim 1, wherein the lysis buffer is a composition of lithium acetate and sodium dodecyl sulphate (SDS).

7. The method of claim 6, wherein the concentration of lithium acetate in the lysis buffer ranges from 0.01M to 0.5M.

8. The method of claim 6, wherein the concentration of sodium dodecyl sulphate in the lysis buffer ranges from 0.1% to 5% v/v or w/v.

9. The method of claim 1, wherein the matrix is a silica coated magnetic bead.

10. The method of claim 1, wherein separating the bound entity from the mixture comprises separating the bound entity from the mixture using a magnet.

11. The method of claim 1, further comprising analyzing the pathogen DNA from the bound entity.

12. The method of claim 1, wherein the one or more proteins containing pathogen binding domains are fusion proteins containing the pathogen binding domains of innate, acute, or innate and acute phase proteins.

13. The method of claim 12, wherein the one or more proteins are coated onto a substrate of paramagnetic bead.

* * * * *